United States Patent [19]

Russell-Jones et al.

[11] Patent Number: 5,449,720

[45] Date of Patent: Sep. 12, 1995

[54] AMPLIFICATION OF THE $VB_{12}$ UPTAKE SYSTEM USING POLYMERS

[75] Inventors: Gregory J. Russell-Jones, Middle Cove; Steven W. Westwood, Ashfield; Alison R. Gould, Erskineville; Bernard V. McInerney, Carlton, all of Australia

[73] Assignee: Biotech Australia PTY Limited, Roseville, Australia

[21] Appl. No.: 64,892

[22] Filed: May 24, 1993

[51] Int. Cl.$^6$ .................. C08F 283/00; C08G 63/91; A01N 33/02

[52] U.S. Cl. ..................... 525/54.1; 530/812; 530/815; 530/816; 424/484; 424/485; 424/486; 424/487; 424/488; 514/656

[58] Field of Search ............. 525/54.1; 530/811, 812, 530/815, 816; 424/484, 485, 486, 487, 488; 514/656

[56] References Cited

U.S. PATENT DOCUMENTS

| | | | |
|---|---|---|---|
| 4,968,742 | 11/1990 | Lewis et al. | 525/54.1 |
| 5,206,219 | 4/1993 | Desai | 514/3 |
| 5,225,182 | 7/1993 | Sharma | 424/9 |
| 5,258,453 | 11/1993 | Kopecek et al. | 525/54.1 |
| 5,308,889 | 5/1994 | Rhee et al. | 525/54.1 |

FOREIGN PATENT DOCUMENTS

| | | |
|---|---|---|
| 2546474 | 4/1977 | Germany. |
| 87/02251 | 4/1987 | WIPO. |
| WO90/04606 | 5/1990 | WIPO. |
| WO93/06767 | 6/1990 | WIPO. |
| WO92/17167 | 10/1992 | WIPO. |
| WO87/02251 | 12/1993 | WIPO. |
| WO93/25221 | 12/1993 | WIPO. |

OTHER PUBLICATIONS

Rihova et al., "Biological Properties of Targetable Poly[N-(2-Hydroxypropyl)Methyacrylamide]-Antibody Conjugates," *J. Control Rel.* 2:289–310 (1985).

Rejmanova et al., "Polymers Containing Enzymatically Degradable Bonds, 2 Poly[N-(2-hydroxypropyl)methacrylamide] Chains Connected by Oligopeptide Sequences Cleavable by Chymotrypsin," *Makoromol. Chem.* 182: 1899–1915 (1981).

Schneider et al., *Comprehensive $B_{12}$*, Verlag Walter de Gruyter & Co., New York, 1987. (Index only).

*Primary Examiner*—Nathan M. Nutter
*Attorney, Agent, or Firm*—Foley & Lardner

[57] ABSTRACT

The invention relates to the oral delivery of peptide and protein pharmaceuticals using the vitamin $B_{12}$ ($VB_{12}$) uptake system, with the delivery being amplified using polymers. More particularly, the invention concerns a complex having the general formula:

$$(V-Q)_n-P-(Q'-A)_m$$

where, V is a carrier which will bind to natural intrinsic factor (IF) selected from vitamin $B_{12}$ or an analogue thereof, n is the molar substitution ratio of V in the complex, and is a number from 1.0 to about 10, P is a pharmaceutically acceptable polymer, A is a pharmaceutically active substance, m is the molar substitution ratio of A in the complex, and is a number greater than 1.0 to about 1000, Q and Q' are independently a covalent bond, or a spacer compound linking V, P and A by covalent bonds.

32 Claims, No Drawings

AMPLIFICATION OF THE VB₁₂ UPTAKE SYSTEM USING POLYMERS

BACKGROUND OF THE INVENTION

The invention relates to the oral delivery of peptide and protein pharmaceuticals using the vitamin $B_{12}$ ($VB_{12}$) uptake system. More particularly the invention relates to the amplification of the uptake system using polymers.

The oral route of administration of peptides such as LHRH and its analogues, or proteins such as Granulocyte Colony Stimulating Factor (GCSF), Erythropoietin (EPO) and insulin, as pharmaceuticals in the treatment of systemic conditions has in the past met with little success. In general, the amount of peptide required for successful oral administration has been 100 to 1000 times the dose required for parenteral delivery, thus making the administration of these agents via this route prohibitively expensive. There are two fundamental reasons for the lack of success. Firstly, the intestinal milieu has a high degree of proteolytic activity, which rapidly degrades most peptides. Secondly, while there are well defined uptake mechanisms for individual amino acids and di-peptides, there is no general mechanism for polypeptides to be transported across the membrane of the mucosal epithelium into the circulation. Rather, this membrane is designed as a general barrier prohibiting the uptake of the numerous foreign proteins encountered in this environment. Thus, although a peptide may be modified to withstand the enzymatic barrage encountered in the intestine, such modification is of little value if the peptide cannot subsequently cross the mucosal barrier and enter the systemic circulation.

Recent work by the current inventor, which is described in PCT Patent Application PCT/AU86/00299 (WO87/02251), has however provided a method to overcome the mucosal barrier. This method takes advantage of the natural intrinsic factor (IF) mediated uptake mechanism for vitamin $B_{12}$ ($VB_{12}$). $VB_{12}$ is a naturally occurring dietary molecule which is actively taken up from the intestine. During this process it first binds to intrinsic factor (IF) in the upper small intestine. The [$VB_{12}$-IF] complex passes down the small intestine and binds to an IF receptor located on the surface of the ileal epithelium. The whole [$VB_{12}$-IF-Receptor] complex is then internalized by receptor-mediated endocytosis and some time later the $VB_{12}$ appears in serum.

PCT Application PCT/AU86/00299 (WO87/02251) describes methods to modify chemically $VB_{12}$ to provide suitable functional groups for conjugation of the $VB_{12}$ to various drugs and peptide/protein pharmaceuticals. When the [$VB_{12}$-pharmaceutical] complex is administered orally it is possible to utilise the natural IF-mediated $VB_{12}$-uptake system to deliver the pharmaceutical to the circulation.

One major limitation to this general $VB_{12}$ uptake mechanism is that the dose of pharmaceutical which can be delivered per feed to the recipient is low. The dose is directly proportional to the amount of $VB_{12}$ which can be taken up per feed. Thus, in mice and rats it is only possible to deliver around 20–40 pMoles of pharmaceutical per dose, while in humans the quantity of pharmaceutical which can be delivered is approximately 1 nMole. While this level of uptake is sufficient to deliver pharmaceutically active doses of some substances, such as LHRH agonists, calcitonin and EPO, it is not sufficient to deliver proteins such as GCSF and insulin at quantities large enough to have a pharmacological effect. It would therefore be desirable to amplify the uptake capacity of the $VB_{12}$ transport system, by at least 10 fold.

Amplification can occur by the linkage of the pharmaceutical to a polymer backbone to which a small number of $VB_{12}$ molecules are linked, either subsequently, previously or at the same time. Preferably the linkage to the polymer, or the polymer to which the pharmaceutical is linked, should be biodegradable.

Potentially biodegradable polymers include dextran and its derivatives and amino acid polymers such polylysine, or poly-(glutamic acid). Non-biodegradable polymers include poly[N-(2-hydroxypropyl)-methacrylamide], to which is attached biodegradable side chains such as those containing ester linkages, or amino acid sequences cleavable within lysosomal vacuoles, ie, Gly-Phe-Leu-Gly (SEQ ID NO:1)(Rihova, B. and J. Kopecek. 1985 Biological properties of targetable poly[[N-(2-hydroxypropyl)-methacrylamide]-antibody complexes. *J. Control Rel.*, 2:289–310). Other amino acid spacers cleavable by intracellular proteases include Gly-Phe-Ala; Gly-Phe-Ala-Gly; (SEQ ID NO:2) Gly-Phe-Tyr-Ala; (SEQ ID NO:3) and Gly-Phe-Tyr-Ala-Ala (SEQ ID NO:4) (Rejmanova, P., Obereigner, B., Kopecek, J. 1981 *Makromol. Chem.* 182: 1899–1915).

Polymers with pendant groups linked to the backbone via spacers containing aromatic diazo bonds are known. Many of these polymers have been designed specifically to release the pendant side groups following cleavage of the diazo bond by azo-reductases released by bacteria in the colon. These polymers however have proven to be unsuitable for delivering drugs systemically following oral administration, because these polymer-drug complexes are not absorbed intact from the intestine, but rather deliver their drug to the colon, following cleavage of the diazo bond by colonic enzymes. Small amounts of the released drug may eventually reach the circulation, but the amount which reaches the circulation has been found to be of little practical value.

Polymers to which are conjugated various cytotoxic drugs are also known. These polymers have been targeted to cancer cells using specific antibodies or sugar moieties. Once the drug-polymer has reached its target tissue the complex is endocytosed by the target cell and the pendant drug is released by the action of lysosomal enzymes, or by cleavage of a disulfide linked drug by intracellular glutathione. Oral delivery of such complexes has not, however, resulted in significant uptake of the drug-polymer complex from the intestinal lumen into the circulation.

SUMMARY OF THE INVENTION

It is the object of this invention to describe a new set of drug/pharmaceutical-polymer conjugates, to which a $VB_{12}$ molecule, or analogue or derivative thereof, has been conjugated. These $VB_{12}$-polymer-drug conjugates are suitable for oral delivery, as they can utilize the aforementioned $VB_{12}$-transport system for uptake and have the added advantage of increasing the amount of pharmaceutical agent which can be delivered via the $VB_{12}$ uptake mechanism.

The complexes of the present invention have the general formula:

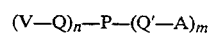

$$(V-Q)_n-P-(Q'-A)_m$$

wherein, V is a carrier, which will bind to natural intrinsic factor (IF), selected from vitamin $B_{12}$ or an analogue thereof, and n, the molar substitution ratio of V in the complex, is a number from 1.0 up to about 10, and P is a pharmaceutically active polymer, and A is a pharmaceutically active substance, and m, the molar substitution ratio of A in the complex, is a number greater than 1.0 up to about 1000, and Q and Q' are independently a covalent bond, or a spacer compound linking V, P and A by covalent bonds.

DESCRIPTION OF THE PREFERRED EMBODIMENTS

The polymer, P, of the present invention can be any pharmaceutically acceptable polymer. The polymer is able to attach to at least one carrier molecule and to at least one, but preferably a multiplicity of active substance molecules.

The polymer P may be a biodegradable polymer, such as a biodegradable carbohydrate polymer, or a polymer of amino acids. Otherwise, the polymer may be a non-biodegradable polymer, in which case it preferably has attached biodegradable side chains allowing for covalent linkage to an active substance.

Suitable polymers for substitution with $VB_{12}$ and modification according to the invention, include poly[N-(2-hydroxypropyl)-methacrylamide], dextran, chondroitan sulfate, water soluble polyurethanes formed by covalent linkage of PEG with lysine, poly(glutamic acid), poly(hydroxypropyl-glutamine) and branched chaim polypeptides formed by the dual modification of the α- and ε-amino groups of lysine during the peptide synthesis. Such polymers may have multiple amino-termini, to which can be conjugated a plurality of the pharmaceutical or drug to be delivered. The polymers can also be formed with multiple cysteines, to provide free thiols, or multiple glutamates or aspartates, to provide free carboxyls for conjugation using suitable carbodiimides. Similarly the polymer can contain multiple histidines or tyrosines for conjugation. When the polymer is a branched chain polypeptide, it may also be further modified to provide multiple functional groups for coupling to the active substance.

Some examples of suitable polymers are polysaccharides, including dextran, inulin, cellulose, starch and derivatives thereof; chondroitan sulfate, poly[N-(2-hydroxypropyl)-methacrylamide] and derivatives thereof, styrene-maleic anhydride copolymer, divinylether-maleic anhydride copolymer, polylysine, poly(glutamic acid), poly(hydroxypropyl glutamine), poly(lactic acid), water-soluble polyurethanes formed by covalent linkage of PEG with lysine or other amino acids and branched chain polypeptides.

If the polymer is a branched chain polypeptide, the polymer may in one preferred form have the general sequence:

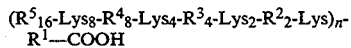
$R^1$—COOH where n is from 1 to 17, $R^1$ is any sequence of from 1 to 10 amino acids, $R^2$, $R^3$, $R^4$, and $R^5$ are each independently any sequence of from 0 to 6 amino acids, providing that not all of $R^2$, $R^3$, $R^4$, and $R^5$ are a sequence of 0 amino acids, and where the polymer may terminate at any position within the brackets. Some examples of polymers having this general formula include the polypeptides with the sequence $(Gly_4-Lys_2-Ser_2-Lys)_5$-Ala-COOH and $(Gly_{16}-Lys_8-Lys_4-His_4-Glu_4-Lys_2-Lys)$-$Gly_5$-Cys-COOH, for example. The terminal amino groups on the end amino acids may be further chemically modified to bond with the active substances, if desired.

The carrier, V, is derived from vitamin $B_{12}$ ($VB_{12}$) or an analogue of vitamin $B_{12}$, which will bind to natural intrinsic factor (IF). The carrier may also be chemically modified in order to bond with the polymer.

Suitable analogues of $VB_{12}$ for derivatization prior to conjugation to the polymer include any variant or derivative of $VB_{12}$ (cyanocobalamin) which possesses binding activity to intrinsic factor. Preferred analogues of $VB_{12}$ also include aquocobalamin, adenosylcobalamin, methylcobalamin, hydroxycobalamin, cyanocobalamin, carbanalide, and 5-methoxybenzylcyanocobalamin [(5-MeO)CN-Cbl] as well as the desdimethyl, monoethylamide and the methylamide analogues of all of the above. Other analogues include all alkyl cobalamins in which the alkyl chain is linked to the corrin nucleus by a direct CoC covalent bond. Other analogues include chlorocobalamin, sulfitocobalamin, nitrocobalamin, thiocyanatocobalamin, benzimidazolecyanocobalamin derivatives such as the: 5,6-dichlorobenzimidazole, 5-hydroxybenzimidazole, trimethylbenzimidazole, as well as adenosylcyanocobalamin [(Ade)CN-Cbl], cobalamin lactone, cobalamin lactam and the anilide, ethylamide, monocarboxylic and dicarboxylic acid derivatives of $VB_{12}$ or its analogues.

Preferred derivatives of $VB_{12}$ also include the mono-, di- and tricarboxylic acid derivatives or the propionamide derivatives of $VB_{12}$. Carriers may also include analogues of $VB_{12}$ in which the cobalt is replaced by zinc or nickel. The corrin ring of $VB_{12}$ or its analogues may also be substituted with any substituent which does not effect its binding to IF, and such derivatives of $VB_{12}$ or its analogues are part of this invention. Other derivatives of $VB_{12}$ or its analogues which have a functional group which is able to react with the spacer compound are also part of the invention. Other derivatives and analogues of vitamin $B_{12}$ are discussed in Schneider, Z. and Stroinski, A.: *Comprehensive $B_{12}$*; (Walter De Gruyter; Berlin, N.Y.; 1987), the disclosure of which is incorporated herein by reference.

The pharmaceutically active substance, A, is any suitable pharmaceutical substance especially a biologically active polypeptide, or a part of this peptide. For example it may be a hormone, growth factor, interleukin, cytokines, lymphokines, or similar substances. Some preferred active substances include GCSF, EPO, LHRH, interferon, or biologically active analogues, parts or derivatives of these substances, calcitonin, TRH, vasopressin, oxytocin, insulin, Growth Hormone, somatostatin, GM-CSF, SCGF, (stem cell growth factor), CGRP or biologically active analogues, parts of derivatives of the above.

Examples of typical substances for delivery according to the invention include active substances such as hormones and bioactive peptides (and analogues and derivatives thereof) such as LHRH, Vasopressin, oxytocin, Insulin, testosterone, interferon, somatotrophin, somatostatin, Erythropoietin, Colony Stimulating factors (GCSF, GM-CSF, CSF), PMSG, HCG, Inhibin, PAI-2: therapeutic agents such as neomycin, salbutamol, pyrimethamine, penicillin G, methicillin, carbenicillin, pethidine, xylazine, ketamine HCl, mephenesin, GABA, iron dextran, nucleotide analogues or ribozyme.

Further examples of active substances include polypeptides such as, insulin, somatostatin, somatostatin derivatives (U.S. Pat. Nos. 4,087,390, 4,100,117 and growth hormones, prolactin, adrenocorticotropic hormone (ACTH), melanocyte stimulating hormone (MSH), thyroid hormone releasing hormone (TRH), its salts, and derivatives thereof (U.S. Pat. No. 4,100,152), thyroid stimulating hormone (TSH), luteinizing hormone (LH), follicle stimulating hormone (FSH), vasopressin, vasopressin derivatives [desmopressin [Folia Endocrinologica Japonica 54, No. 5, p. 676–691 (1978)]], oxytocin, calcitonin, parathyroid hormone, glucagon, gastrin, secretin, pancreozymin, cholecystokinin angiotensin, human placental lactogen, human chorionic gonadotropin (HCG), enkephalin, enkephalin derivatives [U.S. Pat. No. 4,277,394, European patent application Publication No. 31567], endorphin, kyotorphin, interferons ($\alpha$, $\beta$, $\gamma$), interleukins (I, II, and III), tuftsin, thymopoietin, thymosin, thymostimulin, thymic humoral factor (TFH), serum thymic factor (FTS), and its derivatives (U.S. Pat. No. 4,229,438) and other thymic factors [Medicine in Progress 125, No. 10, p.835–843 (1983)], tumor necrosis factor (TNF), colony stimulating factor (CSF), motilin, dinorphin, bombesin, neurotensin, cerulein, bradykinin, urokinase, asparaginase, kallikrein, substance P analogue and antagonist, nerve growth factor, blood coagulation factors VIII and IX, lysozyme chloride, polymixin B, colistin, gramicidin, bacitracin, protein synthesis stimulating peptides (British patent No. 8232082), gastric inhibitory polypeptide (GIP), vasoactive intestinal polypeptide (VIP), platelet-derived growth factor (PDGF), growth hormone factor (GRF, somatocrinin), bone morphogenetic protein (BMP), epidermal growth factor (EGF), etc.

Examples of antitumor agents include bleomycin hydrochloride, methotrexate, actinomycin D, mitomycin C, vinblastine sulfate, vincristine sulfate, daunorubicin hydrochloride, adriamycin, neocarzinostatin, cytosine arabinoside, fluorouracil, tetrahydrofuryl-5-fluorouracil, krestin, picibanil, lentinan, levamisole, bestatin, azimexon, glycyrrhizin, poly I:C, poly A:U and poly ICLC.

Examples of antibiotics, include gentamicin, dibekacin, kanendomycin, lividomycin, tobramycin, amikacin, fradiomycin, sisomicin, tetracycline hydrochloride, oxytetracycline hydrochloride, rolitetracycline, doxycycline hydrochloride, ampicillin, piperacillin, ticarcillin, cephalothin, cephaloridine, cefotiam, cefsulodin, cefmenoxime, cefmetazole, cefazolin, cefotaxime, cefoperazone, ceftizoxime, moxolactam, latamoxef, thienamycin, sulfazecin, and azthreonam.

The aforementioned antipyretic, analgesic and antiinflammatory drugs include, for instance, sodium salicylate, sulpyrine, sodium flufenamate, sodium diclofenac, sodium indomethacin, morphine hydrochloride, pethidine hydrochloride, levorphanol tartrate and oxymorphone.

Examples of the antitussives and expectorants may be mentioned ephedrine hydrochloride, methylephedrine hydrochloride, noscapine hydrochloride, codeine phosphate, dihydrocodeine, phosphate, alloclamide hydrochloride, chlophedianol hydrochloride, picoperidamine hydrochloride, cloperastine, protokylol hydrochloride, isoproterenol hydrochloride, salbutamol sulfate and terbutaline sulfate, Examples of sedatives include chlorpromazine hydrochloride, prochlorperazine, trifluoperazine, atropine sulfate and scopolamine methylbromide. The muscle relaxants include, among others, pridinol methanesulfonate, tubocurarine chloride and pancuronium bromide. The antiepileptics include, for instance, sodium phenytoin, ethosuximide, sodium acetazolamide and chlordiazepoxide hydrochloride. Examples of antiulcer drugs include metoclopramide and L-histidine monohydrochloride. Examples of antidepressants include imipramine, clomipramine, noxiptiline and phenelzine sulfate. The antiallergic drugs include, among others, diphenhydramine hydrochloride, chlorpheniramine maleate, tripelenamine hydrochloride, methdilazine hydrochloride, clemizole hydrochloride, diphenylpyraline hydrochloride and methoxyphenamine hydrochloride. The cardiotonics include among others, trans-p-oxocamphor, theophyllol, aminophylline and etilefrine hydrochloride. The antiarrythmic agents include, for instance propranolol hydrochloride, alprenolol hydrochloride, bufetolol hydrochloride and oxyprenolol hydrochloride. The vasodilators include, among others, oxyfedrine hydrochloride, diltiazem hydrochloride, tolazoline hydrochloride, hexobendine and bamethan sulfate. The antihypertensive diuretics include, among others, hexamethonium bromide, pentolinium, mecamlamine hydrochloride, ecarazine hydrochloride and clonidine hydrochloride. Examples of antidiabetics include sodium glymidine, glypizide, phenformin hydrochloride, buformin hydrochloride and metformin. The anticoagulants include, among others, sodium heparin and sodium citrate.

The haemostatic agents include, among others, thromboplastin, thrombin, menadione sodium bisulfite, acetomenaphthone, $\epsilon$-amino-caproic acid, tranexamic acid, carbazochrome sodium sulfonate and adrenochrome monoaminoguanidine methanesulfonate. Among antituberculotics are isoniazid, ethambutol and sodium p-aminosalicylate. The hormone drugs are exemplified by prednisolone succinate, prednisolone sodium phosphate, dexamethasone sodium sulfate, betamethasone sodium phosphate, hexestrol phosphate, hexestrol acetate and methimazole. The antinarcotic agents include, among others, levallorphan tartrate, nalorphine hydrochloride and naloxone hydrochloride.

If the active substance is GCSF, for example, it can be linked to the polymer with a spacer compound containing a disulfide bond. In this case, the disulfide bond may be formed with the buried thiol group of the cysteine at position 17 in the polypeptide chain of GCSF.

When the active substance is a LHRH analogue, it may be ANTIDE or an analogue of ANTIDE. ANTIDE is a linear decapeptide containing a number of unnatural and/or D-amino acids in addition to three L-amino acid residues. Its N-terminus is acetylated and the C-terminus amidated. ANTIDE has the following sequence:

N-Ac-D-Nal(2), D-Phe(pCl), D-Pal(3), Ser, Lys(-Nic), D-Lys(Nic), Leu, Lys(iPr), Pro, D-Ala-NH$_2$
[Nal(2) represents 3-(2-napthyl) alanine; Phe(p-Cl) represents 3-(4-chlorophenyl)alanine: Pal(3) represents 3-(3-pyridyl)alanine; Lys(Nic) represents N-nicotinoyllysine; Lys-(iPr) represents N-isopropyllysine].

For ANTIDE-1 the residue 6 is D-Lys, not D-Lys(-Nic); for ANTIDE-2 the residue 5 is Lys, not Lys(Nic); and for ANTIDE-3 the residue 8 is Lys, not Lys(iPr).

When the active substance is a LHRH analogue, it may also be histrellin, D-Lys$_6$-LHRH, D-Lys$_6$-LHRH-ethylamide, or an analogue of these substances.

The spacer compounds Q and Q' are optional. When they are absent the carrier V and/or the active substance A are linked to polymer P by a direct covalent bond. They are introduced either to improve the intrinsic factor affinity of the $VB_{12}$ complex or to overcome problems in the coupling of the carrier, V and/or the active substance A arising from unfavourable steric interactions between the V and/or A with the polymer P or to increase the bioactivity of A in the complex. The spacer compounds may also act as linking agents, being bi-functional compounds with selected functional groups on each end to react with suitable functional groups located on the polymer, and also the $VB_{12}$ carrier molecule and/or on the pharmaceutically active substances.

The spacer compound Q and/or Q' preferably comprises optionally substituted saturated or unsaturated, branched or linear, $C_{1-50}$ alkylene, cycloalkylene or aromatic group, optionally with one or more carbons within the chain being replaced with N, O or S, and wherein the optional substituents are selected from, for example, carbonyl, carboxy, hydroxy, amino and other groups.

Suitable extended spacers for the conjugation of the pharmaceutical (A) or the carrier (V) to the polymer matrix (P) include: disuccinimidyl suberate (DSS), bis(-sulfosuccinimidyl) suberate (BSS), ethylene glycolbis(-succinimidylsuccinate) (EGS), ethylene glycolbis(sulfosuccinimidylsuccinate) (Sulfo-EGS), p-aminophenylacetic acid, dithiobis(succinimidylpropionate) (DSP), 3,3'-dithiobis-(sulfosuccinimidylpropionate) (DTSSP), disuccinimidyl tartarate (DST), disulfosuccinimidyl tartarate (Sulfo-DST), bis[2-(succinimidooxycarbonyloxy)-ethylene]sulfone (BSOCOES), bis[2-(sulfosuccinimidooxycarbonyloxy)-ethylene]sulfone (Sulfo-BSOCOES), dimethyl adipimidate.2HCl (DMA), dimethyl pimelimidate.2HCl (DMP), dimethyl suberimidate.2HCl (DMS).

Suitable cross-linking agents for use in the preparation of thiol-cleavable biodegradable spacers or linkers include N-succinimidyl 3-(2-pyridyldithio)propionate (SPDP), iminothiolane, sulfosuccinimidyl-6-[3-(2-pyridyldithio) propionamido]-hexanoate (Sulfo-LC-SPDP), succinimidyl-6-[3-(2-pyridyldithio)propionamido]-hexanoate (LC-SPDP), sulfosuccinimidyl 6-[α-methyl-α-(2-pyridyldithio)toluamido]-hexanoate (Sulfo-LC-SMPT), 1,4-di[3'-(2'-pyridyldithio)propionamido]-butane (DPDPB), 4-succinimidyloxycarbonyl-α-methyl-α-(2-pyridyldithio)-toluene (SMPT), dimethyl 3,3'dithiobispropionimidate.2HCl (DTBP).

In the formula, n, the average molar substitution ratio of V in the complex, is a number from 1.0 to about 10. Preferably n is between 1.0 and 1.2. The polymer is ideally linked to one V carrier molecule, but as the polymer is of uncertain size and/or structure, the number n represents a statistical average. Also, in the formula, m, the average molar substitution ratio of A in the complex, represents a number from at least 1.0 to about 1000. In order to amplify the uptake of the active ingredient m should be as large as possible, ideally between about 10 to 100. m is also a statistical average, and different numbers of active molecules (A) will be bound to the polymer, because of the variation in the polymeric structure of P.

The invention concerns a complex which comprises more than one active substance linked to a polymer, which is linked to at least one carrier molecule which is a $VB_{12}$ molecule, or analogue thereof, wherein the ability of the carrier to undergo the binding reactions necessary for uptake and transport of the $VB_{12}$ in a vertebrate host and the activity of the active substance are substantially maintained, following conjugation or following biological release of the active substance from the polymer. The complex, having the general formula $$(V-Q)_n-P-(Q'-A)_m$$

where V, Q, P, Q', A, n and m are as defined previously, is prepared by one of the following methods:
a) reacting A with P to form an intermediate complex, and thereafter reacting the intermediate complex with V;
b) reacting V with P to form an intermediate complex and thereafter reacting the intermediate complex with A;
c) the process of step a) or b) wherein one or more of V, P or A are modified to provide at least one functional group capable of forming a chemical linkage prior to coupling with the other reactants; or
d) reacting one or two V, P or A with Q and/or Q' prior to coupling with the other reactants.

In general terms, the process may comprise one or more of the following steps:
a) reacting the active substance with the polymer to form said complex;
b) chemically modifying the active substance to provide at least one functional group capable of forming a chemical linkage, and reacting the active substance and polymer to form said complex;
c) chemically modifying the carrier to provide at least one functional group capable of forming a chemical linkage and reacting the carrier and polymer to form said complex;
d) chemically modifying the active substance and the polymer to provide functional groups capable of forming a chemical linkage, and reacting the active substance and polymer to form said complex;
e) reacting the active substance with at least one cross-linking agent and reacting the active substance with the polymer to form said complex;
f) reacting the carrier with at least one cross-linking agent and reacting the polymer and carrier to form said complex;
g) reacting the active substance and polymer with at least one cross-linking agent and reacting the active substance and polymer to form said complex;
h) reacting the active substance directly with a polymeric support to form an intermediate containing a plurality of molecules of the active substance linked to the polymer, and subsequently coupling to the polymer-active substance intermediate one or more carrier molecules;
i) coupling at least one carrier molecules directly to a polymeric support to form an intermediate containing at least one molecule of the, carrier linked to the polymer, and subsequently reacting the active substance to the, polymer-carrier intermediate to a plurality of active substance molecules.

The invention also provides a method for the modification of a polymeric support to introduce functional groups capable of reacting either directly with the active substance or with a chemically-modified form of the active substance. The resulting polymer-active substance intermediate contains one or more molecules of the active substance, said intermediate being suitable for coupling to the carrier to give a complex capable of amplified delivery of the active substances.

In one embodiment of the invention the linkage joining the pharmaceutical, or the carrier to the polymer is a disulfide bond. In a further embodiment of the invention the linkage joining the pharmaceutical, or the carrier to the polymer is an ester linkage. In yet another embodiment of the invention the linkage joining the pharmaceutical or the carrier to the polymer is a γ-glutamyl-ε-lysine bond. In yet another embodiment of the invention the linkage joining the pharmaceutical or the carrier to the polymer is a diazo-linkage. In a preferred embodiment of the invention there is a complex comprising multiple molecules of GCSF linked through a disulfide bond by reaction with a (dithiopyridyl-propionamido)dodecylamine-derivative of the polymer. In another preferr the invention there is a complex comprising multiple molecules of GCSF linked through a disulfide bond to a (dithiopyridyl-propionamido)-dodecylsuberylhexyl-derivative of the polymer.

It has been found that it is possible to synthesize three, analogues of ANTIDE (LHRH antagonist) which are suitable for conjugation to a polymer matrix, namely:

N-Ac-D-Nal(2), D-Phe(pCl), D-Pal(3), Ser, Lys(-Nic), D-Lys, Leu, Lys(iPr), Pro, D-Ala-NH$_2$ (D-Lys$_6$ANTIDE or ANTIDE-1);

N-Ac-D-Nal(2), D-Phe(pCl), D-Pal(3), Ser, Lys, D-Lys(Nic), Leu, Lys(iPr), Pro, D-Ala-NH$_2$ (Lys$_5$-ANTIDE or ANTIDE-2); and N-Ac-D-Nal(2), D-Phe(pCl), D-Pal(3), Ser, Lys(-Nic), D-Lys(Nic), Leu, Lys, Pro, D-Ala-NH$_2$ (Lys$_8$ANTIDE or ANTIDE-3).

The invention also concerns a pharmaceutical composition which comprises a complex as described previously together with a pharmaceutically acceptable carrier or excipient. The composition may be in the form of a capsule, tablet, slow release dosage form, elixir, gel, paste, or enterically coated dosage form, for example, or any other suitable dosage form. A method for the treatment of disease is also part of the invention, which comprises administering to a subject a therapeutically effective amount of a complex as described above, preferably in form of a pharmaceutical composition.

EXAMPLE 1

Synthesis of Multi-Lysine polymer 1 (MLP1)

A multi-Lysine polymer (MLP1) of the general formula (Gly$_4$-Lys$_2$-Ser$_2$-Lys]$_5$-Ala-COOH, was synthesized on an Applied Biosystems peptide synthesiser. More precisely this can be represented as (Gly$_4$-Lys$_2$-Ser$_2$-Lys)$_4$(Gly$_4$-Lys$_2$-Ser$_2$-Lys)-Ala-COOH. The formula of (Gly$_4$-Lys$_2$-Ser$_2$-Lys)$_5$-Ala-COOH can be represented as follows:

which shows the structure more precisely. If necessary the terminal amino-groups on the glycine can be further chemically modified.

EXAMPLE 2

Synthesis of Multi-Lysine polymer 2 (MLP2)

A multi-Lysine polymer (MLP2) of the general formula (Gly$_{16}$-Lys$_8$-Lys$_4$-His$_4$-Glu$_4$-Lys$_2$-Lys)-Gly$_5$-Cys-COOH was synthesized on an Applied Biosystems peptide synthesiser. More precisely the structure can be represented as follows:

```
⎡ Gly⎯⎲                                                        ⎤
⎢      Gly—Lys⎲                                                 ⎥
⎢ Gly⎯⎲        ⎲                                                ⎥
⎢      Gly—Lys—Lys—His—Glu⎲                                     ⎥
⎢ Gly—Lys⎲                  ⎲                                   ⎥
⎢ Gly⎯⎯⎱  ⎲                                                     ⎥
⎢      Gly—Lys—Lys—His—Glu—Lys⎲                                 ⎥
⎢ Gly⎯⎯⎱                        ⎲                               ⎥
⎢                                                               ⎥
⎢ Gly⎯⎲                           ⎲                             ⎥
⎢      Gly—Lys—Lys—His—Glu—Lys—Lys—Gly⎥Cys—COOH                 ⎥
⎢ Gly⎯⎲                          ⎱                              ⎥
⎢      Gly—Lys⎯⎱                ⎱                               ⎥
⎢      Gly—Lys—Lys—His—Glu⎱                                     ⎥
⎢ Gly⎯⎯⎱                  ⎱                                     ⎥
⎢      Gly—Lys⎱                                                 ⎥
⎣ Gly⎯⎯⎱                                                        ⎦
```

EXAMPLE 3

Production of adipyl-hydrazide derivative of eVB$_{12}$ carboxylate

The adipyl-hydrazide derivative of eVB$_{12}$ carboxylate was prepared for conjugation to the terminal carboxyl groups of the polymer by reaction with EDAC. The adipyl-hydrazide derivatives used can be represented by the following (shorthand) chemical structure: adipyl-hydrazido-eVB$_{12}$ (=eVB$_{12}$-CONHNH-CO(CH$_2$)$_4$CONHNH$_2$)

This reagent was readily prepared in one step from eVB$_{12}$ carboxylate by the addition of EDAC to a mixture of the acid and a 20-fold excess of adipylhydrazide; ie:

$$eVB_{12}CO_2H \xrightarrow[EDAC]{20 \text{ eq. adipyl hydrazide}} eVB_{12}CONHNHCO(CH_2)_4CONHNH_2$$

```
Gly———CONH
         |
        (CH2)4
         |
Gly———CONH⎱   ⎲CONH———Ser———CONH
    Gly———CONH                |
         |                  (CH2)4
        (CH2)4                |
Gly———CONH⎱   ⎲CONH———Ser———CONH⎱   ⎲CONH———Ala———COOH
```

EXAMPLE 4

Formation of Polymer-ANTIDE conjugates using non-cleavable homobifunctional cross-linkers.

Previous experiments have shown that the direct conjugation between ANTIDE-1 and ANTIDE-3 and $VB_{12}$ produced conjugates with greatly reduced bioactivity when compared to ANTIDE. The close proximity of the $VB_{12}$ to ANTIDE using this conjugation strategy presumably sterically interferes with the binding of ANTIDE to the LHRH receptor. In order to reduce the steric effect possibly seen with direct conjugation, bifunctional, non-biodegradable linkers, must be used to produce covalent complexes between the two polymers and ANTIDE-1 and 3. As an example, ANTIDE-1 or ANTIDE-3 were reacted with a 1.5 molar excess of Disuccinimidyl suberate (DSS) for 10 minutes at Room Temperate (RT). MLP1 or MLP2 was then added and the reaction allowed to proceed overnight. Conjugated material was purified by chromatography on Sephadex G-25 in 10% acetic acid, followed by Reversed Phase HPLC (RP-HPLC). The Polymer-Anilido-ANTIDE-1 and ANTIDE-3 conjugates were formed by reaction of MLP 1 or MLP 2 with p-aminophenylacetic acid using EDAC/NHS. The Polymer-anilide, was in turn conjugated to ANTIDE-1 and ANTIDE-3 using DSS. The conjugated material was purified by G-25 chromatography in 10% acetic acid followed by RP-HPLC.

$eVB_{12}$ was linked to the polymer ANTIDE complexes by reacting adipyl-hydrazidyl-"e"$VB_{12}$ with the complex using EDAC. The reacted product was purified by RP-HPLC.

EXAMPLE 5

Formation of MLP-ANTIDE conjugates using thiol-cleavable cross-linkers.

Conjugates were also prepared in which the covalent linker contained a biodegradable disulfide bond, which would be reduced in vivo, presumably by glutathione in serum. Briefly, MLP1 or MLP2 was reacted with N-succinimidyl 3-(2-pyridyldithio)propionate (SPDP). The dithiopyridyl-MLP (DTP-MLP) product was purified by RP-HPLC. A free thiol was introduced onto ANTIDE-1 by reaction with SPDP. The dithiopyridyl group was then reduced with mercapto-ethanol and the product purified by RP-HPLC. Similarly, a free thiol was introduced into ANTIDE-3 by reaction with iminothiolane. The thiolated product (SH-HN+ANTIDE-3) was purified by RP-HPLC. Formation of the disulfide linked MLP-ANTIDE-1 and MLP-ANTIDE-2 conjugates was achieved by reaction of the thiolated ANTIDE derivative with DTP-MLP in 2.5% acetic acid for 24 hours. The conjugated material was purified by Sephadex G-25 chromatography, followed by RP-HPLC.

$VB_{12}$ was linked to the polymer-ANTIDE complexes by reacting adipyl-hydrazidyl-"e"$VB_{12}$ with the complex using EDAC. The reacted product was purified by RP-HPLC.

EXAMPLE 6

Conjugation of GCSF to MLP1

Multiple copies of G-CSF were linked to MLP1 by preparing a (dithiopyridyl-propionamido) derivative of a 12-aminododecylamino-substituted MLP1 prepared by reacting diaminododecane with MLP1 using disuccinimidyl suberate (DSS). The substituted MLP1 was reacted with N-succinimidyl-3-(2-pyridyldithio)propionate (SPDP). The dithiopyridyl-MLP1 (DTP-MLP1) product was purified by RP-HPLC. This DTP derivatized-MLP1 was then conjugated to GCSF by a thiol insertion reaction of the free thiol at $Cys_{17}$ of GCSF into the disulfide present on the MLP1 analogue.

$eVB_{12}$ is then linked to the polymer-GCSF complex by reacting adipyl-hydrazidyl $eVB12$ with the complex using EDAC. The reacted product is purified by RP-HPLC.

EXAMPLE 7

Conjugation of GCSF to MLP2

Multiple copies of G-CSF were linked to MLP2 by preparing a (dithiopyridyl-propionamido) derivative of a 12-aminododecylaminosubstituted MLP2 prepared by reacting diaminododecane with MLP2 using disuccinimidyl suberate (DSS). The substituted MLP2 was reacted with N-succinimidyl 3-(2-pyridyldithio)propionate (SPDP). The dithiopyridyl-MLP2 (DTP-MLP2) product was purified by RP-HPLC. This DTP derivatized-MLP2 was then conjugated to G-CSF by a thiol insertion reaction of the free thiol at $Cys_{17}$ of G-CSF into the disulfide present on the MLP2 analogue.

$VB_{12}$ was linked to the polymer-G-CSF complexes by reacting adipyl-hydrazidyl-"e"$VB_{12}$ with the complex using EDAC. The reacted product was purified by RP-HPLC.

EXAMPLE 8

Preparation of poly-GCSF-HPMA-$VB_{12}$ complex

Two N-(2-Hydroxypropyl)methacrylamide (HPMA) copolymers can be synthesized as polymer backbones for the incorporation of GCSF and derivatization with $VB_{12}$. A non-biodegradable polymer backbone (HPMA-GG) was synthesized by the free radical copolymerization of HPMA with N-methacryloylglycylglycine p-nitrophenyl ester. A biodegradable polymer (HPMA-GFALG) was synthesized by the free radical copolymerization of HPMA with N-methacryloylglycylphenylalanylleucylglycine p-nitrophenol ester by the method of Rejmanova and co-workers (Rejmanova, P., Obereigner, B., and Kopecek, J. 198,1 *Makromol. Chem.* 1.82: 1899–1915). In order to incorporate GCSF and $VB_{12}$ onto the polymers, they can be reacted with a ten molar excess of a mixture of aminododecyl-$eVB_{12}$ and dithiopyridyldodecylsuberylhexylamine (1:10 mole:mole) overnight. Unreacted nitrophenyl esters can be subjected to aminolysis by the addition of 1-amino-2-propanol. The modified polymers are purified by chromatography on Sepharose 6B. A solution of the dithiopyridyl-dodecylsuberylhexyl modified $VB_{12}$-substituted polymers is dissolved in 2.5% acetic acid and reacted with GCSF. The reaction mixture is left for 144 hours at 4° C., after which the GCSF-$VB_{12}$-substituted polymers are purified by chromatography on Sepharos 6B.

EXAMPLE 9

Preparation of poly-EPO-HPMA-$VB_{12}$ complex

Two N-(2-Hydroxypropyl)methacrylamide (HPMA) copolymers can be synthesized as polymer backbones for the incorporation and derivatization with EPO and $VB_{12}$. A non-biodegradable polymer backbone (HPMA-GG) can be synthesized by the free radical copolymerization of HPMA with N-methacryloylglycylglycine p-nitrophenyl ester. A biodegradable polymer (HPMA-GFALG) can be synthesized by the free radical copolymerization of HPMA with N-methacryloylglycylphenylalanylleucylglycine p-nitrophenol ester by the method of Rejmanova and co-workers (Rejmanova,P., Obereigner, B., and Kopecek, J. 1981, *Makromol. Chem.* 182 1899–1915). EPO and $VB_{12}$ are incorporated onto the polymers by reaction with a ten molar excess of a mixture of aminododecyl-e$VB_{12}$ and 6-(3-acylhydrazidylpropionamido)-1-amino3,4-dithiahexane (1:10 mole:mole) overnight. Unreacted nitrophenyl esters are then subjected to aminolysis by the addition of 1-amino-2-propanol. The modified polymers can be purified by chromatography on Sepharose 6B. EPO is subsequently covalently linked to the 6-(3-acylhydrazidylpropionamido)-1-amino-3,4-dithiahexane modified $VB_{12}$-substituted polymers by the addition of EDAC. Following reaction for 18 hours at 4° C., the EPO-$VB_{12}$-substituted polymers are purified by chromatography on Sepharose 6B.

We claim:

1. A complex having the general formula $$(V-Q)_n-P-(Q'-A)_m$$

wherein, V is a carrier which will bind to natural intrinsic factor (IF) selected from the group of carriers consisting of vitamin $B_{12}$, an analogue of vitamin $B_{12}$, and a vitamin $B_{12}$ derivative, and n is the molar substitution ratio of V in the complex, and is a number from 1.0 to about 10, and P is a pharmaceutically acceptable polymer, and A is a pharmaceutically active compound, and m is the molar substitution ratio of A in the complex, and is a number greater than 1.0 to about 1000, and Q and Q' are independently a covalent bond, or a spacer compound linking V, P and A by covalent bonds.

2. The complex according to claim 1, wherein at least one of Q and Q' is a spacer compound which contains a biodegradable portion.

3. The complex according to claim 2 wherein said biodegradable portion is selected from a disulfide bond, ester linkage, γ-glutamyl-ε-lysine linkage, or a diazo bond.

4. The complex according to claim 1, wherein n is from 1.0 to about 1.2 and m is from 2 to about 200.

5. The complex according to claim 1, wherein n is from 1.0 to about 1.2, and m is from 10 to 100.

6. A complex according to claim 1 wherein said P is a biodegradable polymer.

7. A complex according to claim 1 wherein said polymer is non-biodegradable.

8. A complex according to claim 7 wherein said non-biodegradable polymer has attached biodegradable side chains for covalent linkage to an active substance.

9. A complex according to claim 1 wherein said polymer is selected from: the polysaccharides comprising dextran, inulin, cellulose, starch and derivatives thereof; chondroitan sulfate, poly[N-(2-hydroxypropyl)-methacrylamide] and derivatives thereof; styrene-maleic anhydride copolymer; divinylether-maleic anhydride copolymer; polylysine, poly(glutamic acid), poly(hydroxypropyl glutamine); poly(lactic acid); water-soluble polyurethanes formed by covalent linkage of PEG with lysine or other amino acids; and branched chain polypeptides.

10. A complex according to claim 9 wherein said polymer is poly[N-2(2-hydroxypropyl)-methacrylamide].

11. A complex according to claim 1 wherein said spacer compound Q or Q' comprises an optionally substituted saturated or unsaturated, branched or linear, $C_{1-50}$ alkylene, cycloalkylene or aromatic group, optionally with one or more carbons within the chain being replaced with N, O or S, and wherein the optional substituents are selected from carbonyl, carboxy, hydroxy, amino and other groups.

12. A complex according to claim 11 wherein said spacer compound is derived frown disuccinimidyl suberate (DSS), bis(sulfosuccinimidyl) suberate (BSS), ethylene glycolbis(succinimidylsuccinate) (EGS), ethylene glycolbis(sulfosuccinimidylsuccinate) (sulfo-EGS), p-aminophenylacetic acid, dithiobis(succinimidylpropionate) (DSP), 3,3-'diothibis(sulfosuccinimidyl tartarate (sulfo-DST), bis[(2-succinimidooxycarbonyloxy)-ethylene]sulfone (BSOCOES), bis[2-(sulfosuccinimidooxycarbonyloxy)-ethylene]sulfone (sulfo-BSOCOES), bis-(sulfosuccinimidooxycarbonyloxy)-ethylene]sulfone (sulfo-BSOCOES), dimethyl adipimidate.2HCl (DMAA), dimethyl pimelimidate.HCl (DMP and dimethyl suberimidate.2HCl (DMS).

13. A complex according to claim 1 wherein said spacer compound is thio-cleavable.

14. A complex according to claim 13 wherein said thiol-cleavable spacer is derived from N-succinimidyl-3-(2-pyridyldithio)propionate (SPDP), iminothiolane, sulfosuccinimidyl-6-[3-(2-pyridyldithio)-propionamido]-hexanoate (sulfo-LC-SPDP), succinimidyl-6-[3-(2-pyridyldithio)-propionamido]hexanoate (LC-SPDP), sulfosuccinimidyl-6-[α-methyl-α-(2-pyridyldithio )-toluamido]-hexanoate (sulfo-LC-SMPT), 1,4-di[3'-(2'-pyridyldithio)priopionamido]-butane (DPDPB), 4-succinimidyloxycarbonyl-α-methyl-α-(2-pyridyldithio)toluene (SMPT) and dimethyl-3,3'dithiobispropionimidate.2HCl (DTBP).

15. A complex according to claim 1 wherein said active substance A is a biologically active polypeptide or a part thereof.

16. A complex according to claim 15 wherein said polypeptide is a hormone, growth factor, interleukin.

17. A complex according to claim 15 wherein said polypeptide is selected from GCSF, EPO, LHRH, or interferon or a part thereof or an analogue thereof.

18. A complex according to claim 17 wherein GCSF is linked to said polymer via a spacer compound Q' containing a disulfide bond.

19. A complex according to claim 18 wherein a disulfide bond is formed between said Q' and the buried thiol of the cysteine at position 17 of the polypeptide chain of GCSF.

20. A complex according to claim 1 wherein said carrier V is selected from cyanocobalamin, aquocobalamin, adenosylcobalamin, methylcobalamin, hydroxycobalamin, cyanocobalamin carbanalide, 5-methoxylbenzylcobalamin, and the desdimethyl, monoethylamide and methylamide analogues of all of the preceding analogues, as well as coenzyme B12, 5'-deoxyadenosylcobalamin, chlorocobalamin, sulfitocobalamin, nitrocobalamin, thiocyanatocobalamin, 5,6-dichlorobenzimadazole, 5-hydroxybenzimidazole, trimethylbenzimidazole, adenosylcyanocobalamin, cobalaminlactone, cobalamin lactam and the anilide; ethylamide, propionamide; monocarboxylic and dicarboxylic acid derivatives of $VB_{12}$ or its analogues; or alkyl cobalamins in which the alkyl chain is linked to the corrin nucleus by a direct CoC covalent bond.

21. A complex according to claim 1 wherein the carrier is a vitamin $B_{12}$ analogue in which the Co is replaced by Ni or Zn.

22. A complex according to claim 20 wherein the carrier is a vitamin $B_{12}$ analogue in which the corrin ring is substituted with a substituent which does not effect binding to intrinsic factor.

23. A process for the production of a complex having the general formula

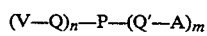

wherein V, Q, P, Q', A, n and m are as defined in claim 1, said process selected from:

a) reacting A with P to form an intermediate complex, and thereafter reacting the intermediate complex with V;

b) reacting V with P to form an intermediate complex and thereafter reacting the intermediate complex with A;

c) the process of step a) or b) wherein one or more of V, P or A are modified to provide at least one functional group capable of forming a chemical linkage prior to coupling with the other reactants; or d) reacting one or two V, P or A with Q and/or Q' prior to coupling with the other reactants.

24. A process according to claim 23 wherein Q and/or Q' comprises an optionally substituted saturated or unsaturated, branched or linear, $C_{1-50}$ alkylene, cycloalkylene or aromatic group, optionally with one or more carbons within the chain being replaced with N, O or S, and wherein the optional substituents are selected from carbonyl, carboxy, hydroxy, amino and other groups.

25. A process according to claim 23 wherein Q' is a cleavable cross-linking agent containing a disulfide bond.

26. A process according to claim 23 wherein the cross-linking agents are selected from disuccinimidyl suberate (DSS), bis(sulfosuccinimidyl) suberate (BSS), ethylene glycolbis(succinimidylsuccinate) (EGS), ethylene glycolbis(sulfosuccinimidylsuccinate) (Sulfo-EGS), p-amino-phenylacetic acid, dithiobis(succinimidylpropionate) (DSP), 3,3'-dithiobis(sulfosuccinimidylpropionate) (DTSSP), disuccinimidyl tartarate (DST), disulfosuccinimidyl tartarate (Sulfo-DST), bis[2-(succinimidyloxycarbonyloxy)ethylene]sulfone(BSOCOES), bis[2-(sulfosuccinimidooxycarbonyloxy)-ethylene]sulfone (Sulfo-BSOCOES), dimethyl adipimidate.2 HCl (DMA), dimethyl pimelimidate.2HCl (DMP), dimethyl suberimidate.2HCl (DMS).

27. A process according to claim 23 wherein said spacer is selected from disuccinimidyl suberate (DSS), bis(sulfosuccinimidyl) suberate (BSS), ethylene glycolbis(succinimidylsuccinate) (EGS), ethylene glycolbis(sulfosuccinimidylsuccinate) (Sulfo-EGS), p-aminophenylacetic acid, dithiobis(succinimidylpropionate) (DSP), 3,3'-dithiobis(sulfosuccinimidylpropionate) (DTSSP), disuccinimidyl tartarate (DST), disulfosuccinimidyl-tartarate (Sulfo-DST), bis[2-(succinimidyloxycarbonyloxy)-ethylene]sulfone (BSOCOES), bis[2-(sulfosuccinimidooxycarbonyloxy)-ethylene]-sulfone (Sulfo-BSOCOES), dimethyl adipimidate.2HCl (DMA), dimethyl pimelimidate.2HCl (DMP), dimethyl suberimidate.2HCl (DMS).

28. A process according to claim 23 wherein said spacer is selected from N-succinimidyl 3-(2-pyridyldithio)propionate (SPDP), iminothiolane, sulfosuccinimidyl 6-[3-(2-pyridyldithio) propionamido]hexanoate (Sulfo-LC-SPDP), succinimidyl 6-[3-(2-pyridyldithio) propionamido]hexanoate (LC-SPDP), sulfosuccinimidyl 6-[-methyl-(2pyridyldithio) toluamido]hexanoate (Sulfo-LC-SMPT), 1,4-di[3'-(2'-pyridyldithio ) propionamido]butane (DPDPB), 4-succinimidyloxycarbonyl-α-methyl-α-(2-pyridyldithio)-toluene (SMPT), dimethyl 3,3'dithiobispropionimidate.2HCl (DTBP).

29. A process according to claim 23 wherein the cross-linking agents are selected from N-succinimidyl 3-(2-pyridyldithio)propionate (SPDP), iminothiolane, sulfosuccinimidyl 6-[3-(2-pyridyldithio) propionamido]-hexanoate (Sulfo-LC-SPDP), succinimidyl 6-[3-(2-pyridyldithio) propionamido]-hexanoate (LC-SPDP), sulfosuccinimidyl 6-[α-methyl-α-(2-pyridyldithio)-toluamido]hexanoate (Sulfo-LC-SMPT), 1,4-di[3'-(2'-pyridyldithio)propionamido]butane (DPDPB), 4-succinimidyloxycarbonyl-α-methyl-α-(2-pyridyldithio)-toluene (SMPT), dimethyl 3,3'dithiobispropionimidate.2HCl (DTBP).

30. A pharmaceutical composition which comprises a complex according to claim 1 together with a pharmaceutically acceptable carrier or excipient.

31. A composition according to claim 29 in the form of a capsule, tablet, slow release dosage form, elixir, gel, paste, or enterically coated dosage form.

32. A complex according to claim 1, wherein said complex is capable of binding to intrinsic factor thereby enabling uptake and transport of the complex from the intestinal lumen of a vertebrate host via intrinsic factor to the systemic circulation of said host.

* * * * *

UNITED STATES PATENT AND TRADEMARK OFFICE
CERTIFICATE OF CORRECTION

PATENT NO. : 5,449,720
DATED : September 12, 1995
INVENTOR(S) : Russell-Jones et al.

It is certified that error appears in the above-indentified patent and that said Letters Patent is hereby corrected as shown below:

On the title page:

"32 Claims" should read —43 Claims—

The following claims should be added:

Signed and Sealed this

Fifth Day of December, 1995

Attest:

BRUCE LEHMAN

*Attesting Officer*

*Commissioner of Patents and Trademarks*

UNITED STATES PATENT AND TRADEMARK OFFICE
CERTIFICATE OF CORRECTION

PATENT NO. : 5,449,720
DATED : September 12, 1995
INVENTOR(S) : Russell-Jones et al.

It is certified that error appears in the above-indentified patent and that said Letters Patent is hereby corrected as shown below:

33. A complex according to claim 6 wherein said biodegradable polymer is selected from a biodegradable carbohydrate polymer or a polymer of amino acids.

34. A polymer according to claim 9 wherein said polymer is a branched chain polypeptide optionally modified to provide multiple functional groups for coupling of an active substance.

35. A complex according to claim 34 wherein said polymer has the sequence:
$(R^5_{16}\text{-Lys}_8\text{-}R^4_6\text{-Lys}_4\text{-}R^3_4\text{-Lys}_2\text{-}R^2_2\text{-Lys})_n\text{-}R^1\text{-COOH}$
where n is from 1 to 17, $R^1$ is any sequence of from 1 to 10 amino acids, $R^2$, $R^3$, $R^4$, and $R^5$ are each independently any sequence of from 0 to 6 amino acids, providing that not all of $R^2$, $R^3$, $R^4$, and $R^5$ are a sequence of 0 amino acids, and where the polymer may terminate at any position within the brackets.

36. A complex according to claim 35 wherein said polymer has the sequence of $(\text{Gly}_4\text{-Lys}_2\text{-Ser}_2\text{-Lys})_5\text{-Ala-COOH}$.

37. A complex according to claim 35 wherein said polymer has the sequence of $(\text{Gly}_{16}\text{-Lys}_8\text{-Lys}_4\text{-His}_4\text{-Glu}_4\text{-Lys}_2\text{-Lys})\text{Gly}_5\text{-Cys-COOH}$.

38. A complex according to claim 17 wherein said LHRH analogue is histrellin, or an analogue of histrellin.

39. A complex according to claim 17 wherein said LHRH analogue is $\text{D-Lys}_6\text{-LHRH}$.

40. A complex according to claim 17 wherein said LHRH analogue is $\text{D-Lys}_6\text{-LHRH-ethylamide}$.

41. A complex according to claim 17 wherein said LHRH analogue is ANTIDE or an analogue of ANTIDE.

42. A complex according to claim 40 wherein said ANTIDE analogue is $\text{D-Lys}_6\text{-ANTIDE}$.

43. A complex according to claim 40 wherein said ANTIDE analogue is $\text{Lys}_8\text{-ANTIDE}$.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly Phe Leu Gly
    1

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Gly Phe Ala Gly
    1

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly Phe Tyr Ala
    1

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly Phe Tyr Ala Ala
    1                5